(12) United States Patent
Boström

(10) Patent No.: US 6,203,506 B1
(45) Date of Patent: Mar. 20, 2001

(54) OPERATING DEVICE FOR A STYLET UNIT

(75) Inventor: Mats Boström, Sundbyberg (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/242,193

(22) PCT Filed: Jul. 16, 1997

(86) PCT No.: PCT/SE97/01291

§ 371 Date: Mar. 13, 2000

§ 102(e) Date: Mar. 13, 2000

(87) PCT Pub. No.: WO98/07465

PCT Pub. Date: Feb. 26, 1998

(30) Foreign Application Priority Data

Aug. 16, 1996 (SE) .................................................. 9602998

(51) Int. Cl.$^7$ .................................................. A61B 5/00
(52) U.S. Cl. .................................................. 600/585
(58) Field of Search .................................. 600/433–436, 600/585

(56) References Cited

U.S. PATENT DOCUMENTS

| | | | |
|---|---|---|---|
| 4,858,810 | 8/1989 | Intlekofer et al. | 226/127 |
| 5,170,787 | 12/1992 | Lindegren | 128/642 |
| 5,396,902 | 3/1995 | Brennen et al. | 128/772 |
| 5,752,915 | 5/1998 | Neubauer et al. | 600/373 |

FOREIGN PATENT DOCUMENTS

| | | |
|---|---|---|
| 0 050 606 | 4/1982 | (EP) . |
| 0 368 330 | 5/1990 | (EP) . |
| 0 534 737 | 3/1993 | (EP) . |
| 0 773 036 | 5/1997 | (EP) . |

*Primary Examiner*—Max Hindenburg
(74) *Attorney, Agent, or Firm*—Schiff Hardin & Waite

(57) ABSTRACT

A device for manipulating a stylet unit having a stylet movable within a stylet sleeve, for positioning an electrode cable in a body cavity, has first and second relatively movable parts, with an interface area wherein respective surfaces of the first and second parts are in contact with each other. A groove is disposed in one of these surfaces and receives the stylet unit, with the stylet being connected to one of the first and second parts, and the stylet sleeve being connected to the other of the first and second parts.

14 Claims, 2 Drawing Sheets

OPERATING DEVICE FOR A STYLET UNIT

BACKGROUND OF THE INVENTION

1. Field of the Invention

The present invention relates to a device for manipulating a stylet unit, of the type having a stylet sleeve and a stylet located therein, for positioning an electrode cable in a body cavity. In particular, the invention is directed to a device of this type having first and second parts which are movable relative to each other, one of which receives and holds the proximal end of the stylet and the other of which receives and holds the proximal end of the stylet sleeve, and a support and guide structure for a proximal section of the stylet which projects beyond the end of the stylet sleeve when the stylet and stylet sleeve are moved relative to each other.

2. Description of the Prior Art

A device for operating a stylet unit of the above kind for achieving a desired stiffening of an electrode cable during its advancement into a body cavity, e.g. via a vein into the atrium of the heart, and a desired final position for the distal end of the electrode cable by providing the cable with a bent L- or J-like shape is disclosed in U.S. Pat. No. 5,170,787. Here, the distal end of the stylet is pre-bent and is kept retracted inside the stylet sleeve during the electrode cable's insertion phase, giving the distal end of the electrode cable an essentially straight shape, the stylet, in the final positioning of the distal end of the electrode cable, being exposed outside its tubular sleeve to cause the distal end of the electrode cable to assume the desired curved shape. In order to achieve the exposure of the pre-bent distal end of the stylet outside its tubular sleeve, U.S. Pat. No. 5,170,787 proposes a device which either moves the stylet distally in relation to a stationary sleeve or moves the tubular sleeve proximally in relation to a stationary stylet. In principle, the latter option is preferable, since it does not entail any movement of the electrode cable in relation to the stylet unit's operating device. The known operating device comprises two stiff tubes, one telescoping inside the other, in order to obtain a stiffening that prevents the stylet from buckling when its free proximal end is slid distally inside the tubular sleeve respectively when the tubular sleeve is slid proximally over the free proximal end of the stylet in the operating device. This means that the operating device's total linear elongation is relatively large, since the total length of the telescoping tubes must be twice the length of the stylet's stroke in relation to the tubular sleeve.

An operating device for a stylet unit of the initially cited kind is disclosed in European Application 773 036 in which the stiff, telescoping tubes of the operating device according to U.S. Pat. No. 5,170,787 are replaced by a compressible helical spring which supports the free, proximal end of the stylet and which, in turn, is guided with a tight fit in an elongate cavity in a handle housing. In this way the total length of the operating device can be shortened considerably while the number of device parts could be reduced, resulting in lower manufacturing costs for the operating device.

SUMMARY OF THE INVENTION

An object of the present invention is to provide an operating device of the initially mentioned kind which can be even shorter, have even fewer parts and, accordingly, be made cheaper than previously proposed devices while retaining the requisite strength and reliability.

The above object is achieved in a device for manipulating a stylet unit of the type initially described wherein the device includes an arrangement for supporting and guiding the proximal section of the stylet which projects beyond the end of the stylet sleeve, when the stylet and the stylet sleeve are moved relative to each other, formed by a groove located in one of the relatively movable parts, this groove enclosing the stylet and being disposed in the surface of one of the relatively movable parts at an interface area of that surface which is in contact with the other relatively movable part. Therefore, in the inventive device the stiff, telescoping control tubes or the stylet guiding spring in previously proposed operating devices are not needed and are replaced by a simple stylet groove at the interface between both main parts of the operating device.

The shortest total length for the operating device is achieved when one of its parts is devised as a rotatingly supported roller body in a handle section in which the stylet and stylet sleeve are able to traverse a non-linear path when the stylet and stylet sleeve are moved in relation to one another when the configuration of the distal end of the electrode cable is to be changed.

DESCRIPTION OF THE PREFERRED EMBODIMENTS

Preferred embodiments

Figure 1:
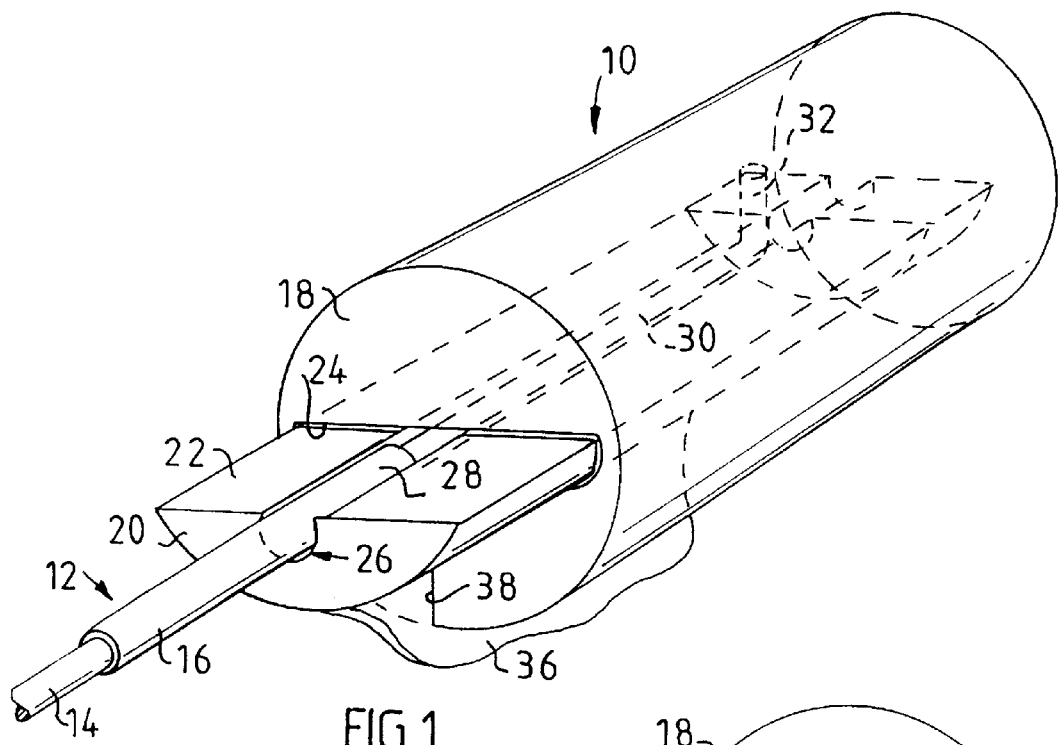
FIG. 1 is a schematic perspective view of an operating device with linear operation according to a first embodiment of the present invention.

FIG. 1 shows a schematic view of an embodiment, generally designated 10, of a device according to the invention for manipulating a stylet unit 12 during the introduction and implantation of an electrode cable (not shown) in a body cavity, such as through a vein into the right atrium of the heart, for the purpose of achieving the desired stiffening of the electrode cable during its introduction and achieving the desired positioning and configuration, e.g. a J shape, for the distal end of the electrode cable. The operating device 10 according to the invention is therefore intended for manipulating a stylet unit 12 of the kind comprising an internal stylet 14 enclosed in a tubular sleeve 16, both the sleeve 16 and the stylet 14 being intended for insertion into the central channel of the electrode cable for stiffening the cable during its introduction and for bending the distal end thereof into the desired shape. For this purpose, the distal end section of the internal stylet 12 is pre-bent in the known manner but enclosed inside the tubular sleeve 16 during the electrode cable's advancement in order to keep the distal end of the stylet unit 12 and, accordingly, the electrode cable essentially straight. When the distal end of the electrode cable has been maneuvered into e.g. the right atrium of the heart, the tubular stylet sleeve 16 can be retracted, whereupon the pre-tensioning of the exposed, pre-bent distal end section of the stylet 14 inside the electrode cable causes the distal end section of the electrode cable to bend into the desired shape, e.g. an L shape or a J shape. Alternately, the stylet can be moved out from the stylet sleeve, but this would result in simultaneous retraction of the electrode cable from the operating device. The operating device 10 according to the invention is therefore designed to guide this movement of the stylet sleeve 16 in relation to the stylet 14.

Figure 2:
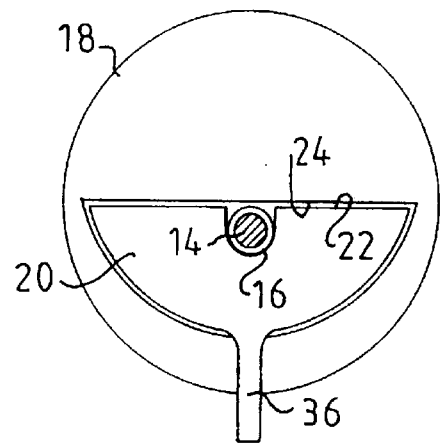
FIG. 2 is an end view of the operating device of FIG. 1.
Figure 3:
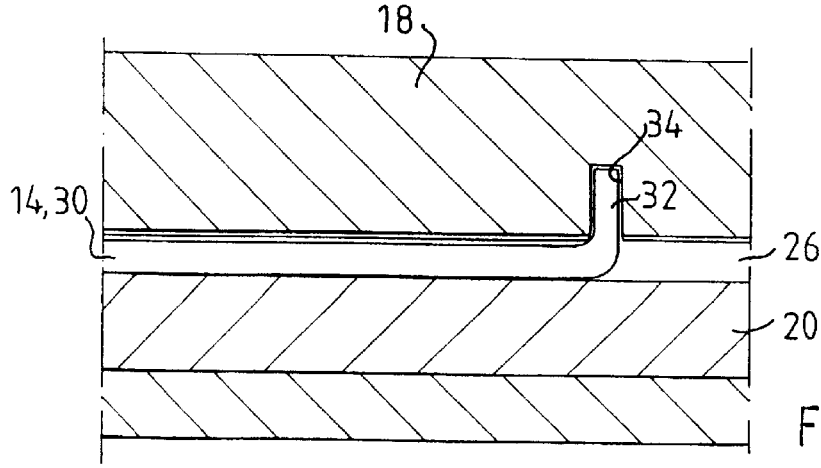
FIG. 3 is a fragmentary, longitudinal sectional view of the operating device of FIG. 1 in the region of the attachment of the stylet to the handle section.

The embodiment of the operating device 10, shown in FIGS. 1–3, according to the invention is of a type with linear operation and comprises, in principle, a first part, for instance a housing 18 devised as a handle, and a second part, devised as a slide, which is supported so as to be linearly movable into and out from the housing 18. The slide 20 has an upper surface 22 which slides with a tight fit against the opposing surface 24 of a cavity in the housing 18. A groove 26, in which a proximal end section 28 of the stylet sleeve 16 is attached, is made on the upper surface 22 of the slide 20. A proximal end section 30 of the stylet 14, which projects from this end section 28, extends to the rear in the groove 26 to an attachment point at which the end of the stylet 32 is bent up and fastened in a perpendicular blind hole 34 opening onto the groove 26 in the housing 8, as best shown in FIG. 3. The groove 26 and the opposite surface 24 accordingly form a guide channel which encloses the stylet 14 with a relatively tight fit, preventing it from buckling when the slide 20 and stylet sleeve 16 slidingly are withdrawn to the rear. The slide 20 has a grip section 36, which extends through a slot 38 into the lower part of the housing 18 to facilitate linear movement of the slide 20 in relation to the housing 18.

The operating device according to the embodiment in FIGS. 1–3 operates as follows:

Before the electrode cable is introduced into the body cavity, the stylet unit 12 is fully inserted into the electrode cable with the stylet 14 enclosed by the stylet sleeve 16, i.e. the operating slide 20 is held in a forward, distal end position in the housing 18. When the tubular sleeve's 16 distal end reaches the distal end of the electrode cable, the latter can be inserted into the body cavity, e.g. the right atrium of the heart. When the cable reaches the atrium, the distal end section of the electrode cable is bent into the desired L shape or J shape by retracting the slide 20, i.e. in a proximal direction, with the fingers, the tubular sleeve 14 accompanying the slide 20 and exposing the pre-bent distal end of the stylet 14 at the distal end of the electrode cable, thus bending the cable into the desired shape depending on how much of the bent, distal end of the stylet is exposed. Here, the primary task of the groove 26 is to enclose or stiffen the proximal, free end section 30 of the stylet 14 with a relatively tight fit, thereby preventing buckling thereof due to friction between the stylet 14 and the sleeve 16 when the latter is retracted along the stylet 14.

After the distal end of the electrode cable reaches its final position, it can be actively affixed to the heart wall by manual rotation of a rotation sleeve (not shown), on the proximal end of the slide 20, to which the electrode cable's proximal contact pin is attached.

Within the scope of the present invention, the relative movement of the housing 8 and slide 20 can alternately be reversed in the embodiment according to FIGS. 1–3, i.e. the proximal end of the stylet 14 can be attached to the slide 20, the stylet housing 16 attached to the housing 18 and the groove 26 devised in the housing, the stylet 14 being insertable into and out of a stationary sleeve 16. However, this means that the distance between the distal end of the electrode cable and the operating device 10 would increase when there is distal displacement of the stylet 14, and the proximal end of the electrode cable therefore must be free to follow this movement.

Figure 4:
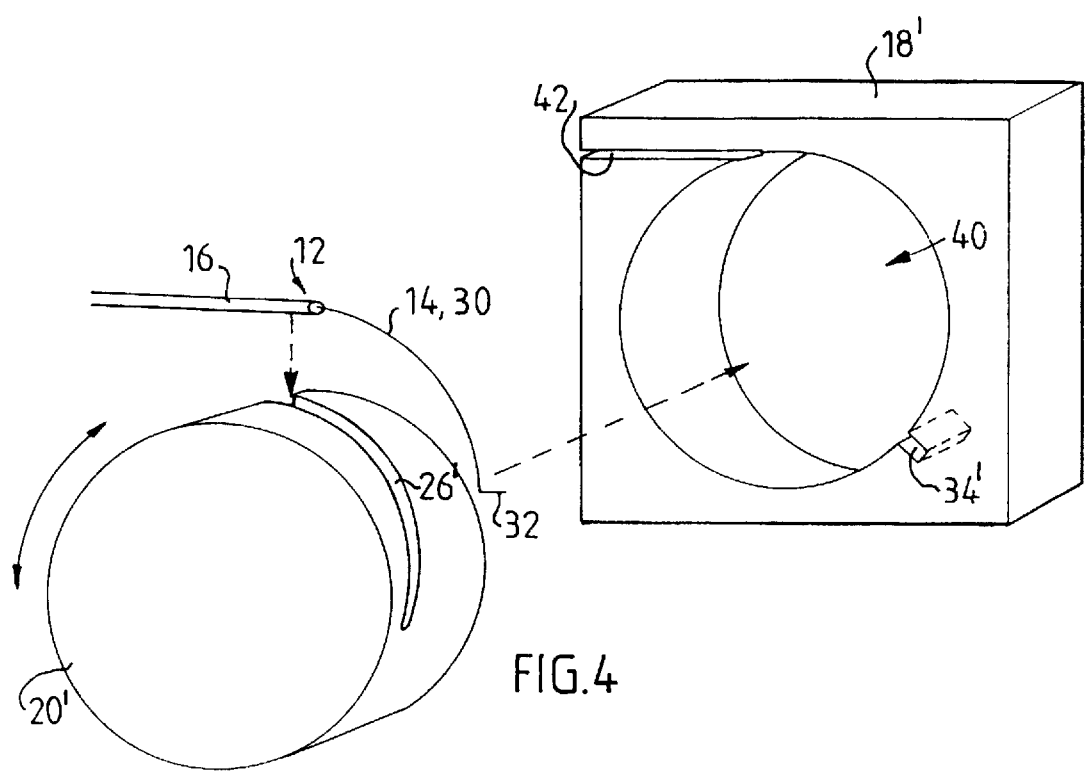
FIG. 4 is a schematic, exploded perspective view of a second embodiment of an operating device in accordance with the invention, with non-linear operation.

FIG. 4 shows a view of an alternative embodiment of the operating device according to the invention, which operates with non-linear relative movement between the stylet and the stylet sleeve. Thus, this embodiment employs a housing 18' in which a roller body 20' is rotatably arranged in a cavity 40 in the housing. The roller body 20' has a peripheral guide groove 26' for the stylet 14, and the housing 18' has a through hole 42 for the proximal end section of the stylet sleeve 16 which is to be fastened to the guide groove 26', The housing 18' further has an attachment point 34', located opposite the stylet groove 26', for the proximal end of the stylet 32. Thus, by rotating the roller body 29' relative to the housing 18', the stylet sleeve 16 can be moved towards the attachment point 34', thereby sliding over the stylet 14, guided so as to prevent stylet buckling in the stylet groove 26', the pre-bent distal end section of the stylet 14 being moved out from the stylet sleeve 16 to the degree required to shape the distal end section of the electrode cable into a suitable J shape. Since non-linear relative motion is achieved between the stylet 14 and the sleeve 16, in this instance, the operating device 16 can be devised with a shorter length.

Figure 5:
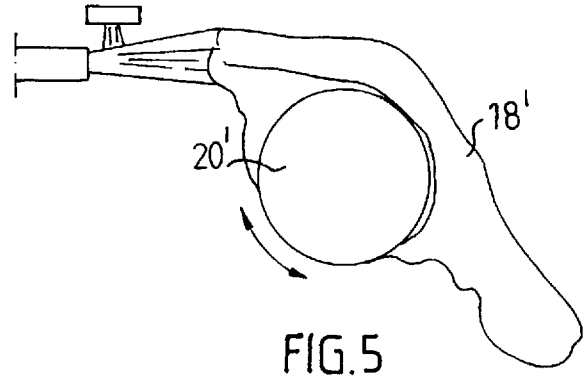
FIG. 5 is a schematic side view of a first practical embodiment of the operating device according to the invention, with non-linear operation.
Figure 6:
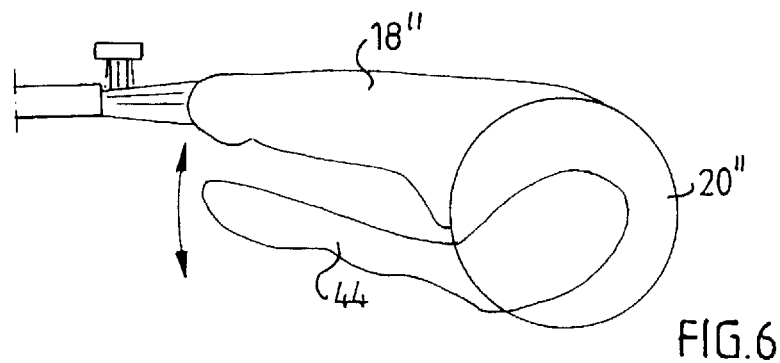
FIG. 6 is a schematic side view of a second practical embodiment of the operating device according to the invention, with non-linear operation.

FIGS. 5 and 6 schematically depict two practical embodiments of a control device according to FIG. 4.

In FIG. 5, the housing 18' has been devised as a handle, so rotation of the roller body 20' can be performed with one finger.

In the embodiment according to FIG. 6, the roller body 20" can be rotated in relation to the handle 18" with a lever 44 in the middle of same, so the stylet unit can be manipulated by manually pressing the lever 44 and handle 18" towards each other. Here, the lever 44 is preferably pretensioned with a spring (not shown) which presses the lever 44 towards an end position away from the housing 18".

In the embodiments according to FIGS. 4–6, the relative movement of the stylet and the stylet sleeve also can be reversed, i.e. the stylet's and sleeve's attachment points and the groove's location in the housing and roller body respectively can change place.

Although modifications and changes may be suggested by those skilled in the art, it is the intention of the inventor to embody within the patent warranted hereon all changes and modifications as reasonably and properly come within the scope of his contribution to the art.

What is claimed is:

1. A device for manipulating a stylet unit having a stylet sleeve and a stylet movable inside said stylet sleeve, for positioning an electrode cable in a body cavity, said stylet sleeve having a proximal end and said stylet having a proximal end, and said stylet having a proximal section which projects beyond said proximal end of said stylet sleeve, said device comprising:

a first part and a second part being in contact with each other and relatively movable with respect to each other at an interface region, said first part having a first part surface in said interface region and said second part having a second part surface in said interface region;

one of said first part and said second part being adapted for connection to said proximal end of said stylet and the other of said first part and said second part being adapted for connection to said proximal end of said stylet sleeve, so that when said first and second parts are moved relative to each other, said proximal region of said stylet is caused to beyond said proximal end of said stylet sleeve; and a groove disposed in one of said first part surface and said second part surface adapted to enclose said proximal region of said stylet for supporting and guiding said proximal region of said stylet outside of said stylet sleeve, said groove being disposed in said interface region.

2. A device as claimed in claim 1 wherein said first part is adapted for connection to said proximal end of said stylet and wherein said second part is adapted for connection to said proximal end of said stylet sleeve, and wherein said first part is supported in and is relatively movable with respect to, said second part.

3. A device as claimed in claim 2 wherein said stylet sleeve has a diameter, and wherein said groove has a depth and a width substantially equal to said diameter of said stylet sleeve.

4. A device as claimed in claim 1 wherein said first part is stationary relative to said second part, and wherein said second part is adapted for connection to said proximal end of said stylet and said first part is adapted for connection to said proximal end of said stylet sleeve.

5. A device as claimed in claim 4 wherein said stylet sleeve has a diameter, and wherein said groove has a depth and a width which is not substantially larger than said diameter of said stylet sleeve.

6. A device as claimed in claim 1 wherein said first part comprises a handle section adapted for holding in a human hand, and wherein said second part comprises a slide which is linearly movable relative to said handle section.

7. A device as claimed in claim 1 wherein said second part comprises a handle section adapted for holding in a human hand, and wherein said first part comprises a slide which is linearly movable relative to said handle section.

8. A device as claimed in claim 1 wherein said first part comprises a handle section adapted for holding in a human hand, and wherein said second part comprises a rotatable body which is rotatable relative to said handle section.

9. A device as claimed in claim 8 wherein said rotatable body comprises a roller body.

10. A device as claimed in claim 9 further comprising a lever interacting said handle section and connected to said roller body for rotating said roller body.

11. A device as claimed in claim 1 wherein said second part comprises a handle section adapted for holding in a human hand, and wherein said first part comprises a rotatable body which is rotatable relative to said handle section.

12. A device as claimed in claim 11 wherein said rotatable body comprises a roller body.

13. A device as claimed in claim 12 further comprising a lever interacting said handle section and connected to said roller body for rotating said roller body.

14. A device as claimed in claim 1 wherein said proximal end of said stylet has a bend of approximately 90° and wherein said one of said first part and said second part is adapted to receive said bend for fastening said proximal end of said stylet to said one of said first part and said second part.

* * * * *